United States Patent [19]

Serpelloni

[11] Patent Number: 4,831,129

[45] Date of Patent: May 16, 1989

[54] DIRECTLY COMPRESSIBLE POWDERED MALTITOL AND ITS PROCESS OF PREPARATION

[75] Inventor: Michel Serpelloni, Bethune, France

[73] Assignee: Roquette Freres, Freres, France

[21] Appl. No.: 913,465

[22] Filed: Sep. 30, 1986

[30] Foreign Application Priority Data

Oct. 2, 1985 [FR] France .................................. 85 14611

[51] Int. Cl.$^4$ ..................... A61K 31/70; A23C 1/236; C07H 15/04

[52] U.S. Cl. ........................................ 536/124; 536/8; 536/4.1

[58] Field of Search .............................. 536/8, 124, 4.1

[56] References Cited

U.S. PATENT DOCUMENTS

| | | | |
|---|---|---|---|
| 3,915,736 | 10/1975 | Oyamada et al. | 426/548 |
| 3,918,986 | 11/1975 | Hiraiwa | 426/661 |
| 4,217,413 | 8/1980 | Walon | 426/658 |
| 4,408,041 | 10/1983 | Hirao et al. | 426/589 |
| 4,652,640 | 3/1987 | Sakai et al. | 536/124 |
| 4,661,647 | 4/1987 | Serpelloni et al. | 568/852 |
| 4,725,387 | 2/1988 | Hirao et al. | 426/48 |

FOREIGN PATENT DOCUMENTS

| | | |
|---|---|---|
| A-0072080 | 2/1983 | European Pat. Off. . |
| A-2236005 | 1/1975 | France . |
| A-2275555 | 1/1976 | France . |
| A-2451357 | 10/1980 | France . |

*Primary Examiner*—Ronald W. Griffin
*Attorney, Agent, or Firm*—Larson and Taylor

[57] ABSTRACT

Directly compressible powdered maltitol having a richness in maltitol higher than 85% by weight and a compressibility, determined in a test A, higher than 80 N.

11 Claims, 1 Drawing Sheet

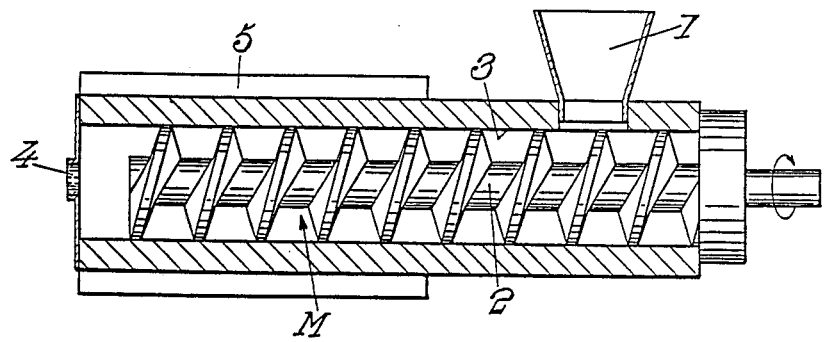

DIRECTLY COMPRESSIBLE POWDERED MALTITOL AND ITS PROCESS OF PREPARATION

The invention relates, as a new industrial product, to directly compressible powdered maltitol.

It also relates to a processing for the preparation of this powdered maltitol.

The sweetening power of maltitol, which is high with respect to that of conventional sugar alcohols such as sorbitol, mannitol and the like, would open numerous applications to maltitol in the field of the pharmaceutical and food industries if it were possible to confer on it acceptable direct compression characteristics.

Discussion has already occured in scientific and trade literature of directly compressible powdered maltitol, with or without granulation binder.

Now in the absence of a binder or binding agent in the granulation step, the compressibility of the product is not very satisfactory.

And the presence of a binder is not very welcome to manufacturers particularly of pharmaceutical products.

The applicant has therefore sought to develop a directly compressible powdered maltitol not including a granulation binder and having improved compressibility properties with respect to those of the product already existing.

And he has had the merit of preparing in fact such a powdered maltitol which is characterized by a richness in maltitol higher than 85% by weight on dry matter and by a compressibility, determined in a test A, higher than 80 N.

Preferably, the richness in maltitol of the above-said novel industrial product is higher than 92% by weight and more preferably still than 95% by weight and its compressibility, determined in the test A, is higher than 100 N.

Test A consists in measuring the strength, expressed in Newtons, typical of the compressibility of the maltitol under examination, which is necessary to cause a tablet prepared from said maltitol to be crushed, i.e. to bring about the formation of rupture lines within the constituent mass thereof, this strength thus reflecting the resistance to crushing of said tablet, which is cylindrical with flat faces, with a diameter of 13 mm, a thickness of 5 mm and a weight of 0.896 g, i.e. having a specific gravity of 1.35 g/ml, the said strength being exerted against the peripheral surface of the tablet in the direction of the axis of revolution thereof by means of a mechanical movable stop applied against said surface along a generatrix, the said tablet being furthermore immobilized against a mechanical stationary stop also applied against the peripheral surface of the tablet along a generatrix, the latter being diametrically opposed to the generatrix against which the mechanical movable stop is applied.

In accordance with the process developed by the applicant to prepare the powdered maltitol constituting the above said novel industrial product, a raw material essentially constituted by powdered maltitol is subjected to an extrusion treatment in a cooking-extrusion installation comprising a heating zone and an extrusion die, the supply flow rate of the installation with raw material as well as the parameters of the extrusion treatment, namely the temperature existing within the heating zone, the diameter of the extrusion die and the moving speed of the raw material within the heating zone being selected so that at the outlet from the die and before its exit from the latter, said maltitol is partly molten.

The powdered maltitol according to the invention is also defined as being a powdered maltitol which is liable to be obtained by the process according to the invention.

Preferably, the above-said installation is of the dual-screw type comprising an extrusion die, the parameters of the extrusion treatment being selected so that the raw material is at a temperature of 100° to 160° C., preferably from 110° to 150° C. inside the die and before the exit of the maltitol from the latter.

Under these conditions, the proportion of molten maltitol is from 30 to 90%, and more generally from 50 to 80%.

The time taken by the maltitol to move through the extrusion installation is advantageously from 0.5 to 10 minutes, preferably from 1 to 4 minutes.

The invention is also directed to other features which are preferably used at the same time and which will be more explicitly considered below and it will, in any case, be well understood by means of the additional description which follows as well as the accompanying drawing and the example, said additional description and example relating to advantageous embodiments.

The single FIGURE of the drawing shows, in diagramatic section, an extrusion installation of the type of those which can be used within the scope of the process according to the invention.

Contemplating, consequently, to manufacture a powdered maltitol according to the invention, directly compressible without the use of a granulation binder, procedure is as follows or in equivalent manner.

The raw material which is subjected to the extrusion treatment according to the invention, is constituted by powdered maltitol essentially in the form of crystalline maltitol.

In practice, native maltitol crystals are used, that is to say crystals obtained by crystallization in water or by solidification of molten maltitol; again in practice, to these native crystals are added, by recycling, the part of the maltitol obtained at the end of the process, which is not commercially useful, for example by reason of a granulometry poorly dapted to the requirements of the market.

The temperature of these crystals is generally comprised, at the inlet of the extrusion installation employed within the scope of the process according to the invention, between 15° and 80° C.

The extrusion installation is constituted advantageously by an extruder of the dual-screw comprising as shown in FIG. 1:

a feed system, particularly a measuring and mixing hopper 1, a malaxating zone M comprising a system including two endless screws 2 arranged inside a casing 3, the said screws consisting particularly of nitrided steel and being driven in rotation by a not shown mechanism, an outlet comprising one or several dies 4 of different shapes, heating means 5 enabling the temperature of the malaxation zone to be controlled, these heating means 5 being constituted, for example, by electrical resistances, by a system of induction heating or by steam and by not shown cooling means arranged outside the casing or inside it and having, for example, the form of coils housed in the casing, of a cooling fluid circuit housed inside the screw, and the like.

The raw material entering through the supply system into the malaxation zone is subjected, due to the compression produced in the turns of the screw, to intense shearing and mechanical friction simultaneously with the heating induced by the heating means.

The extrusion constitutes, consequently, a thermomechanical treatment.

To fix ideas, it is indicated that good results have been obtained with an extruder of the dual-screw type marketed under the name "BC 82" by the CREUSOT-LOIRE company. The two screws intermesh and rotate in the same direction. The malaxation zone is heated by induction and the temperature can hence be easily regulated therein.

The essential advantage of this method of heating is its flexibility of use and its easy control by means of a simple regulation loop (thermocouple/control device of the electrical supply to the induction heating means). It could be that the existence of an intense electromagnetic field exerts an influence on the properties of the product.

In the case of the installation used within the scope of the example described below, the die used was of cylindrical shape and had a diameter of 5 mm.

The temperature of the heating zone is obtained by imposing on the heating system a predetermined value.

In the case of the extrusion installation which has just been considered, this value is comprised between 210° and 280° C., preferably between 240° and 280° C. and, more preferably still, in the vicinity of 260° C.

The mechanical characteristics of the screws and their rotary speed are selected so that the dwell time of the raw material within the heating zone is from 1.5 to 2.5 minutes.

By means of the choice of all of these parameters, the temperature of the raw material which has undergone the treatment, is from 110° to 150° C. inside the die and before its exit from the latter.

The maltitol obtained at the exit of the extrusion installation is successively subjected:
  to cooling,
  to grinding,
  to sifting and
  to recycling of the fines (particles of size too small to be retained by the smallest sieve of the installation) at the level of the suply of the extruder.

Before testing the performance in compression of the maltitol so obtained, a lubricating agent is incorporated with it, in the event magnesium stearate in the proportion generally from 0.5 to 2%.

EXAMPLES

In the following examples, the compressibility is tested of
  two qualities of powdered maltitol according to the invention and of
  four varieties of maltitol powder of the prior art.

To prepare the two qualities of maltitol according to the invention, an extruder of the "BC 82" type considered above is supplied with powdered maltitol.

The speed of the screws is adjusted so that the flow rate of the installation is 250 kg/hour and the passage time of the raw material in the installation is 2 minutes.

The reference temperature of the heating system is programmed to 260° C., which enables the production at the exit of the extruder of maltitol at a temperature varying from 145° to 147° C.

This maltitol is in the form of small rods which are ground by means of a grinder of the hammer type.

By sifting, the fines are separated and recycled to the level of the supply of the extruder.

The fraction retained is of granulometry higher than 50 $\mu$m, more generally than 100 $\mu$m.

The first of the two qualities of powdered maltitol according to the invention, denoted by 1a, is obtained by using as raw material maltitol, crystallized in water, of maltitol richness 98% by weight on dry matter.

The second quality, denoted by 1b, is obtined by using maltitol, crystallized in water, of a richness in maltitol of 95% by weight on dry matter.

The four qualities of powdered maltitol according to the prior art, respectively denoted by 2a, 2b, 2c and 2d, are constituted
  as regards the quality 2a, by maltitol crystallized in water having a chemical purity of 98% by weight,
  as regards the quality 2b, by maltitol crystallized in water having a chemical purity of 95% by weight,
  as regards the quality 2c, by dehydrated massecuite of maltitol having a chemical purity of 92% by weight,
  as regards the quality 2d, by dehydrated massecuite of maltitol having a chemical purity of 85% by weight.

For the six varieties of powdered maltitol tested, the average particle size distribution is determined corresponding to 50% of the distribution by weight.

Their flow index is also measured by resorting to the method of CARR R. L. in Chem. Eng. 72, No. 1, 163–168 (1965) and Chem. Eng. 72, No. 2, 69–73 (1965); to do this, an apparatus known under the trademark "HOSOKAWA POWDER TESTER" and manufactured by MICROMERITICS, Osaka (Japan) is used.

The friability of these six qualities is then determined. This property is characterized as being represented by the percentage of particles which have not withstood crushing in an apparatus called a friabilimeter. In the event, that of the trademark "ERWEKA TA" was used. This apparatus contains 5 identical steel balls of 1.7 cm diameter and 18.87 g each. There is introduced therein 15 g of a granulometric fraction 400 to 500 microns of the powder tested and the apparatus is placed in rotation at 25 r.p.m. for 15 minutes. There is determined by weight, at the end of the crushing, the proportion, expressed in percent, represented by the residue retained by a sieve of mesh width of 351 microns; the value of the friability corresponds to the complement to 100 of the latter value. The greater the figure so obtained, the greater the friability.

Finally, the compressibility of these six qualities is determined by way of the above-defined test A.

For manufacture of the tablets, recourse may be had to an alternating press of the type type A.M., manufactured by the FROGERAIS company (France). The adjustments of said press are made so that the tablets obtained have a specific gravity of 1.35 g/ml.

To the raw material constituted by the six qualities tested, respectively 1% by weight of lubricant constituted by magnesium stearate, is added.

In the case of the qualities 2a to 2d, one is obliged, in addition, to add for the manufacture of the tablets, a "anti-sticking" agent adapted to prevent the adhesion of the tablets to the forming tools; this antisticking agent may be talc; it is generally added in a proportion of 3 to 7, more generally from 4 to 6% in weight.

The qualities 1a and 1b do not necessitate the presence of an antisticking agent; they are devoid of antisticking agent or at least do not contain an appreciable amount thereof.

The above-said tablets are in the form of cylinders of revolution having the following dimensions:
diameter: 13 mm
height: 5 mm
weight: 0.896 g.

In order to determine, according to test A, the resistance to crushing of the tablets thus prepared, a device called "durometer" is used, for instance the durometer SCHLEUNIGER-2E manufactured in France by FROGERAIS company.

The results of these compressibility measurements as well as the granulometric distribution, the average granulometry, the content of antisticking agent constituted by talc, the indexes of flow and the friability of the six qualities tested, are collected in the table below.

TABLE

| Example (variety of maltitol) | Maltitol powder according to the invention | | Maltitol powder of the prior art | | | |
| --- | --- | --- | --- | --- | --- | --- |
| | 1a | 1b | 2a | 2b | 2c | 2d |
| Richness in maltitol | 98% | 95% | 98% | 95% | 92% | 85% |
| Talc | 0 | 0 | 4% | 6% | 4% | 6% |
| Flow (CARR) | 79 | 82 | >50 | >50 | 79 | 76 |
| Friability (in %) | 80.7 | 58 | — | — | 48 | 48 |
| Granulometry | Reconstituted | Reconstituted | Reconstituted | Reconstituted | Reconstituted | Reconstituted |
| % fraction > 1000 μm | 0 | 0 | 0 | 0 | 0 | 0 |
| % fraction > 800 μm | 30 | 30 | 30 | 30 | 30 | 30 |
| % fraction > 500 μm | 30 | 30 | 30 | 30 | 30 | 30 |
| % fraction > 315 μm | 30 | 30 | 30 | 30 | 30 | 30 |
| % fraction > 200 μm | 10 | 10 | 10 | 10 | 10 | 10 |
| Granulometry mean (in μm) | 580 | 580 | 580 | 580 | 580 | 580 |
| Compressibility (Breaking strength) in N | 140 | 105 | 41 | measurement impossible | 75 | 52 |

It results from this table that the powdered maltitol according to the invention, (1) has a compressibility or resistance to crushing which is distinctly increased, (2) in no way necessitates, and this is a determining advantage, the addition of an antisticking agent such as talc, the powder obtained after extrusion not resulting in any sticking effect in the manufacture of tablets which is far from being the case the maltitols according to the prior art (it is recalled that talc has a tendency to absorb pharmaceutical active principles whose activity in the tablet is hence diminished).

I claim:

1. Directly compressible powdered maltitol having a richness in maltitol higher than 85% by weight and by a compressiblity, determined in a test A, higher than 80 N, the said test A consisting in measuring the strength, expresed in Newtons, which is necessary to cause a tablet prepared from said maltitol to be crushed, this strength thus reflecting the resistance to crushing of said tablet, which is cylindrical with flat faces, with a diameter of 13 mm, a thickness of 5 mm and a weight of 0.896 g, i.e. having a specific gravity of 1.35 g/ml, the said strength being exerted against the peripheral surface of the tablet in the direction of the axis of revolution thereof by means of a mechanical movable stop applied against said surface along a generatrix, the said tablet being furthermore immobilized against a mechanical stationary stop also applied against the peripheral surface of the tablet along a generatrix, the latter being diametrically opposed to the generatrix against which the mechanical movable stop is applied.

2. Directly compressible powdered maltitol according to claim 1 having a richness in maltitol higher than 92% by weight and a compressibility, determined in test A, higher than 100 N.

3. Directly compressible powdered maltitol according to claim 1 having a richness in maltitol higher than 95% by weight and a compressibility, determined in test A, higher than 100 N.

4. Directly compressible powdered maltitol according to claim 1, free of any antisticking agent in appreciable proportions.

5. Process of manufacturing compressible powdered maltitol according to claim 1, comprising subjecting a raw material essentially constituted by powdered maltitol to an extrusion treatment inside a cooking-extrusion installation comprising a heating zone and an extrusion die, the supply flow rate of the installation in raw material as well as the parameters of the extrusion treatment, namely the temperature existing inside the heating zone, the diameter of the extrusion die and the speed of driving the raw material inside the heating zone being selected so that at the exit of the die and before its exit from the latter, the said maltitol is partly molten.

6. Process according to claim 5, wherein the cooking-extrusion installation is of the dual-screw type comprising an extrusion die, the parameter of the extrusion treatment being selected so that the raw material is at a temperature of 100° to 160° C. inside the die and before the exit of the maltitol from the latter.

7. Process according to claim 5, wherein the cooking-extrusion installation is of the dual-screw type comprising an extrusion die, the parameter of the extrusion treatment being selected so that the raw material is at a temperature of 110° to 150° C. inside the die and before the exit of the maltitol from the latter.

8. Process according to claim 5, wherein the time taken by the maltitol to move through the extrusion installation is from 0.5 to 10 minutes.

9. Process according to claim 5, wherein the time taken by the maltitol to move through the extrusion installation is from 1 to 4 minutes.

10. Process according to claim 5, wherein the time taken by the maltitol to move through the extrusion installation is from 1.5 to 2.5 minutes.

11. Directly compressible powdered maltitol obtained by the process according to claim 5.

* * * * *